(12) United States Patent
Itoi et al.

(10) Patent No.: US 11,016,060 B2
(45) Date of Patent: May 25, 2021

(54) METHOD AND APPARATUS FOR EVALUATING DAMAGE TO MAGNETIC LINEAR BODY

(71) Applicant: TOKYO ROPE MANUFACTURING CO., LTD., Tokyo (JP)

(72) Inventors: Hiroaki Itoi, Tokyo (JP); Sadanori Shiiki, Tokyo (JP); Masamichi Sugahara, Tokyo (JP); Toshiyuki Moriya, Tokyo (JP)

(73) Assignee: TOKYO ROPE MANUFACTURING CO., LTD., Tokyo (JP)

( * ) Notice: Subject to any disclaimer, the term of this patent is extended or adjusted under 35 U.S.C. 154(b) by 187 days.

(21) Appl. No.: 16/427,461

(22) Filed: May 31, 2019

(65) Prior Publication Data

US 2019/0285585 A1 Sep. 19, 2019

Related U.S. Application Data

(63) Continuation of application No. PCT/JP2016/085704, filed on Dec. 1, 2016.

(51) Int. Cl.
*G01R 33/00* (2006.01)
*G01R 33/10* (2006.01)
(Continued)

(52) U.S. Cl.
CPC ............ *G01N 27/83* (2013.01); *G01D 3/022* (2013.01); *G01D 5/145* (2013.01); *G01D 5/202* (2013.01);
(Continued)

(58) Field of Classification Search
CPC ...... G01D 5/145; G01D 11/245; G01D 3/022; G01D 5/202; G01R 33/093; G01R 33/09;
(Continued)

(56) References Cited

U.S. PATENT DOCUMENTS

2008/0061635 A1* 3/2008 Saitou ................. H01F 41/0253
310/13
2010/0254565 A1* 10/2010 Saitou ................. H01F 41/0253
381/400
2015/0028975 A1* 1/2015 Kamiunten ........... F16F 15/035
335/295

FOREIGN PATENT DOCUMENTS

JP S62276454 A 12/1987
JP 03262957 A 11/1991
(Continued)

OTHER PUBLICATIONS

Korean Intellectual Property Office Notice of Preliminary Rejection; May 15, 2020; 9 pgs.; English Language Translation 8 pgs.
(Continued)

*Primary Examiner* — Raul J Rios Russo
(74) *Attorney, Agent, or Firm* — Dickinson Wright PLLC (57) ABSTRACT

A damage evaluation apparatus, to evaluate damage to a tendon embedded in concrete. The apparatus includes a magnetizer for generating magnetic force, and a detector for detecting change in magnetism produced from a damaged area of the tendon when magnetized. The magnetizer includes a excitation coil; an iron core passing through a center hole of the excitation coil; a pair of columnar yokes connected to respective ends of the iron core and extending toward the concrete; and a pair of plate-shaped yokes connected to the pair of columnar yokes at a distal end thereof for forming magnetic poles having spread along the surface of the concrete. By passing an electric current through the excitation coil, a magnetic circuit is formed by the yoke shaft, the pair of columnar yokes, the pair of plate-shaped yokes, and the tendon over a range thereof situated between the pair of plate-shaped yokes.

20 Claims, 5 Drawing Sheets

(51) Int. Cl.

| | | |
|---|---|---|
| *G01N 27/83* | (2006.01) | |
| *G01N 27/80* | (2006.01) | |
| *G01N 27/9013* | (2021.01) | |
| *G01N 33/38* | (2006.01) | |
| *G01R 33/02* | (2006.01) | |
| *G01R 33/12* | (2006.01) | |
| *G01V 3/10* | (2006.01) | |
| *G01N 27/82* | (2006.01) | |
| *G01D 5/14* | (2006.01) | |
| *G01D 11/24* | (2006.01) | |
| *G01D 3/02* | (2006.01) | |
| *G01D 5/20* | (2006.01) | |
| *G01R 33/09* | (2006.01) | |
| *G01R 31/28* | (2006.01) | |
| *G01R 33/06* | (2006.01) | |

(52) U.S. Cl.
CPC ........... *G01D 11/245* (2013.01); *G01N 27/80* (2013.01); *G01N 27/82* (2013.01); *G01N 27/902* (2013.01); *G01N 33/383* (2013.01); *G01R 33/02* (2013.01); *G01R 33/09* (2013.01); *G01R 33/093* (2013.01); *G01R 33/12* (2013.01); *G01V 3/104* (2013.01); *G01R 31/2829* (2013.01); *G01R 33/06* (2013.01)

(58) Field of Classification Search
CPC .... G01R 31/2829; G01R 33/06; G01R 33/02; G01R 33/12; G01R 33/0094; G01R 33/072; G01N 27/83; G01N 27/82; G01N 27/80; G01N 27/902; G01N 33/383; G01V 3/104; G01V 3/081
USPC .................................................. 324/200–263
See application file for complete search history.

(56) References Cited

FOREIGN PATENT DOCUMENTS

| JP | H09113592 A | 5/1997 |
|---|---|---|
| JP | 2002005896 A | 1/2002 |
| JP | 2004279245 A | 10/2004 |
| JP | 2005292111 A | 10/2005 |
| JP | 2007033027 A | 2/2007 |
| JP | 2007064628 A | 3/2007 |
| JP | 3163378 U | 10/2010 |
| JP | 2014062745 A | 4/2014 |

OTHER PUBLICATIONS

JP Office Action (5 pages) and English Language Translation (9 pages), dated Dec. 24, 2019.
Krause, H.-J. et al.; SQUID array for magnetic inspection of prestressed concrete bridges; Physica C, 2002, vol. 368, pp. 91-95.

\* cited by examiner

METHOD AND APPARATUS FOR EVALUATING DAMAGE TO MAGNETIC LINEAR BODY

CROSS REFERENCE TO RELATED APPLICATIONS

This application is a Continuation Application of PCT International Application No. PCT/JP2016/085704 filed on Dec. 1, 2016, the entire disclosure of the application being considered part of the disclosure of this application and hereby incorporated by reference.

TECHNICAL FIELD

The present invention relates to a method and apparatus for evaluating damage (state of deterioration) of a magnetic linear body, typically a magnetic linear body that is embedded in concrete. The linear body includes a cable, rope, strand, cord, wire, rod, pole, shaft or other object in a form extending continuously in one direction, and also includes not only twisted objects but also objects merely bundled together or alone. Further, size of diameter and cross-sectional shape of the body does not matter. The term "magnetic linear body" signifies a linear body produced from a magnetic material, typically a ferromagnetic material.

BACKGROUND ART

Japanese Patent Application (Laid-Open No. 2002-5896) discloses a wire-rope damage detector which attaches a probe coil so as to surround a wire rope.

Here the assumption is that a wire rope to be inspected by the damage inspection apparatus described in the JP Patent Application is a wire rope capable of being surrounded by a probe coil, namely a wire rope exposed to the outside. With the damage detector described in JP Patent Application, a wire rope that has been embedded in concrete cannot be inspected as is embedded in the concrete.

DISCLOSURE OF THE INVENTION

An object of the present invention is to arrange it so that a magnetic linear body embedded in concrete can be inspected as is embedded in the concrete.

A further object of the present invention is to reduce loss of magnetomotive force produced by a magnetizer for the purpose of magnetizing a magnetic linear body that has been embedded in concrete.

A further object of the present invention is to reduce the weight of a damage evaluation apparatus equipped with yokes.

A method of evaluating damage to a magnetic linear body according to a first aspect of the present invention, comprising: moving a damage evaluation apparatus along the magnetic linear body on a concrete structure in which the magnetic linear body, which is to undergo evaluation of damage, is embedded; the apparatus including a magnetizer for generating magnetic force, and a detector for detecting an amount of change in magnetism produced from a damaged area of the magnetic linear body magnetized by the magnetic force generated by the magnetizer; forming a magnetic circuit by passing an electric current through an excitation coil by the magnetizer, wherein the magnetizer includes the excitation coil as well as a yoke shaft inserted into a center hole of the excitation coil; a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, the magnetic circuit including the yoke shaft, the pair of columnar yokes, the pair of plate-shaped yokes and the magnetic linear body over a range thereof situated between the pair of plate-shaped yokes; and detecting magnetic flux, which flows through the magnetic circuit, by the detector. Damage includes abrasion, corrosion, severance and the like.

An apparatus for evaluating damage to a magnetic linear body according to a first aspect of the present invention is used upon being placed on a concrete structure in which the magnetic linear body, which is to undergo evaluation of damage, is embedded, and the apparatus includes a magnetizer for generating magnetic force, and a detector for detecting an amount of change in magnetism produced from a damaged area of the magnetic linear body magnetized by the magnetic force generated by the magnetizer; the apparatus having a moving device, which includes a movement amount sensor, for moving the damage evaluation apparatus along the magnetic linear body; wherein the magnetizer includes an excitation coil, a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, and passes an electric current through the excitation coil, whereby a magnetic circuit is formed by the yoke shaft, the pair of columnar yokes, the pair of plate-shaped yokes and the magnetic linear body over a range thereof situated between the pair of plate-shaped yokes; the detector being a magnetic flux detector for detecting magnetic flux that flows through the magnetic circuit.

In accordance with the first aspect of the present invention, a magnetic circuit is formed that includes in its path the magnetic linear body within the concrete. If the magnetic linear body sustains a reduction in cross-sectional area due to abrasion or corrosion or develops a gap due to severance thereof, magnetic resistance in the magnetic circuit increases and there is a change (reduction) in the magnetic flux that flows through the magnetic circuit. Damage (deterioration) produced in the magnetic linear body embedded in the concrete can be evaluated based upon the change in magnetic flux detected by the magnetic flux detector.

Since the magnetic linear body is embedded in concrete, gaps (portions where there are separations in the magnetic circuit due to the intervention of the concrete) exist between the pair of plate-shaped yokes and the magnetic linear body. The permeability of concrete is comparatively small (substantially the same value as that of the permeability of air) and a decline in the magnetic flux that flows through the magnetic circuit between the pair of plate-shaped yokes and magnetic linear body cannot be avoided. The gaps between the respective pair of plate-shaped yokes and the magnetic linear body can be considered resistance in the magnetic circuit.

In accordance with the first aspect of the present invention, the pair of plate-shaped yokes forming the magnetic poles have spread along the surface of the concrete and hence the cross-sectional area of the gaps is large. The magnetic resistance produced by the gaps is inversely proportional to the cross-sectional area of the gaps. Therefore, by using the plate-shaped yokes of large area as magnetic poles, the cross-sectional area of the gaps is enlarged and, as a result, the magnetic resistance produced in the magnetic circuit by the gaps can be reduced. Loss of magnetomotive force resulting from the fact that the magnetic linear body is embedded in concrete can be reduced and efficiency of utilization of the magnetomotive force improved. Further, since the cross-sectional area of the gaps is enlarged by the plate-shaped yokes, the weight of the damage evaluation apparatus can be lowered in comparison with an arrangement in which the cross-sectional area of the gaps is enlarged using thick columnar yokes, by way of example.

A search coil wound around at least one of the pair of columnar yokes can be used as the detector for detecting the magnetic flux that flows through the magnetic circuit, and so can Hall devices secured to a bottom surface of the plate-shaped yokes.

Preferably, the distance between the pair of plate-shaped yokes (the distance between the magnetic poles) is longer than the distance (gap length) from the bottom surface of the pair of plate-shaped yokes to the magnetic linear body. The magnetic flux that flows directly between the pair of plate-shaped yokes (between the magnetic poles) without passing through the magnetic linear body can be eliminated or reduced. This also contributes to a reduction in loss of magnetomotive force in the magnetic circuit that includes the magnetic linear body.

In an embodiment, the damage evaluation apparatus has a position detecting device for detecting the position of the damage evaluation apparatus relative to the magnetic linear body, path of travel of the damage evaluation apparatus being decided in accordance with an output from the position detecting device. In an embodiment, a plurality of Hall devices having an orientation responsive to magnetic flux along the axial direction of the magnetic linear body can be used as the position detecting device, the Hall devices being arrayed in a row in a direction orthogonal to the direction of the central axis of the excitation coil. Since the damage evaluation apparatus is placed in such a manner that the direction of the central axis of the excitation coil and the axial direction of the magnetic linear body become the same, the direction of the central axis of the excitation coil and the axial direction of the magnetic linear body are basically the same. Magnetic flux in the axial direction is produced in the magnetized magnetic linear body, at the periphery thereof, and the magnetic flux in the axial direction is detected by the plurality of Hall devices having the orientation responsive to the magnetic flux along the axial direction of the magnetic linear body and being arrayed in a row in a direction orthogonal to the central axis of the excitation coil (a direction orthogonal to the axial direction of the magnetic linear body). Typically, the travel path of the damage evaluation apparatus is decided in such a manner that an output signal from a centrally situated Hall device among the plurality of Hall devices arrayed in the row will be maximized, i.e., so as to situate the magnetic linear body at the center of the damage evaluation apparatus along the width direction thereof, and a more stable signal acquisition is achieved.

A method of evaluating damage to a magnetic linear body according to a second aspect of the present invention, comprising: moving a damage evaluation apparatus along the magnetic linear body, on a concrete structure in which the magnetic linear body, which is to undergo evaluation of damage, is embedded, the apparatus including a magnetizer for generating magnetic force, and a detector for detecting an amount of change in magnetism produced from a damaged area of the magnetic linear body magnetized by the magnetic force generated by the magnetizer; forming a magnetic circuit by passing an electric current through an excitation coil by the magnetizer, wherein the magnetizer includes the excitation coil as well as a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, the magnetic circuit including the yoke shaft, the pair of columnar yokes, the pair of plate-shaped yokes and the magnetic linear body over a range thereof situated between the pair of plate-shaped yokes; and detecting magnetic flux, which leaks from the damaged area of the magnetic linear body, by the detector.

An apparatus for evaluating damage to a magnetic linear body according to a second aspect of the present invention is used upon being placed on a concrete structure in which the magnetic linear body, which is to undergo evaluation of damage, is embedded, and includes a magnetizer for generating magnetic force, and a detector for detecting an amount of change in magnetism produced from a damaged area of the magnetic linear body magnetized by the magnetic force generated by the magnetizer; the apparatus having a moving device, which includes a movement amount sensor, for moving the damage evaluation apparatus along the magnetic linear body; wherein the magnetizer includes an excitation coil, a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, and passes an electric current through the excitation coil, whereby a magnetic circuit is formed by the yoke shaft, the pair of columnar yokes, the pair of plate-shaped yokes and the magnetic linear body over a range thereof situated between the pair of plate-shaped yokes; the detector being a leakage flux detector for detecting magnetic flux that leaks from the damaged area of the magnetic linear body.

In accordance with the second aspect of the present invention as well, a magnetic circuit is formed that includes in its path the magnetic linear body within the concrete. Since the pair of plate-shaped yokes forming the magnetic poles have spread along the surface of the concrete and hence the cross-sectional area of the gaps is large, the magnetic resistance produced in the magnetic circuit by the gaps can be reduced. Loss of magnetomotive force resulting from the fact that the magnetic linear body is embedded in concrete can be reduced and efficiency of utilization of the magnetomotive force improved. Further, since the cross-sectional area of the gaps is enlarged by the plate-shaped yokes, the weight of the damage evaluation apparatus can be lowered, If the magnetic linear body is damaged, magnetic flux will leak from the damaged area. According to the second aspect of the present invention, damage (deterioration) that has occurred in the magnetic linear body embedded in concrete can be evaluated based upon leakage flux detected by the leakage flux detector.

In an embodiment, the detector for detecting leakage magnetic flux is provided at a position midway between the pair of plate-shaped yokes (a position midway between the magnetic poles). Since the magnetic field is more stable here in comparison with a location close to either of the pair of plate-shaped yokes, the accuracy with which the leakage magnetic flux is detected can be improved.

With regard also to the detector for detecting leakage magnetic flux, a Hall device can be used and so can a search coil.

In an embodiment, a plurality of the Hall devices having an orientation responsive to magnetic flux in the radial direction of the magnetic linear body are arrayed in a row in a direction orthogonal to the direction of the central axis of the excitation coil. Since magnetic flux generated from a damaged area will include a large component in the radial direction of the magnetic linear body, magnetic leakage flux can be detected more accurately by placing a plurality of the Hall devices in such an attitude as to have an orientation responsive to the magnetic flux along the radial direction of the magnetic linear body.

DETAILED DESCRIPTION OF THE INVENTION

Figure 1:
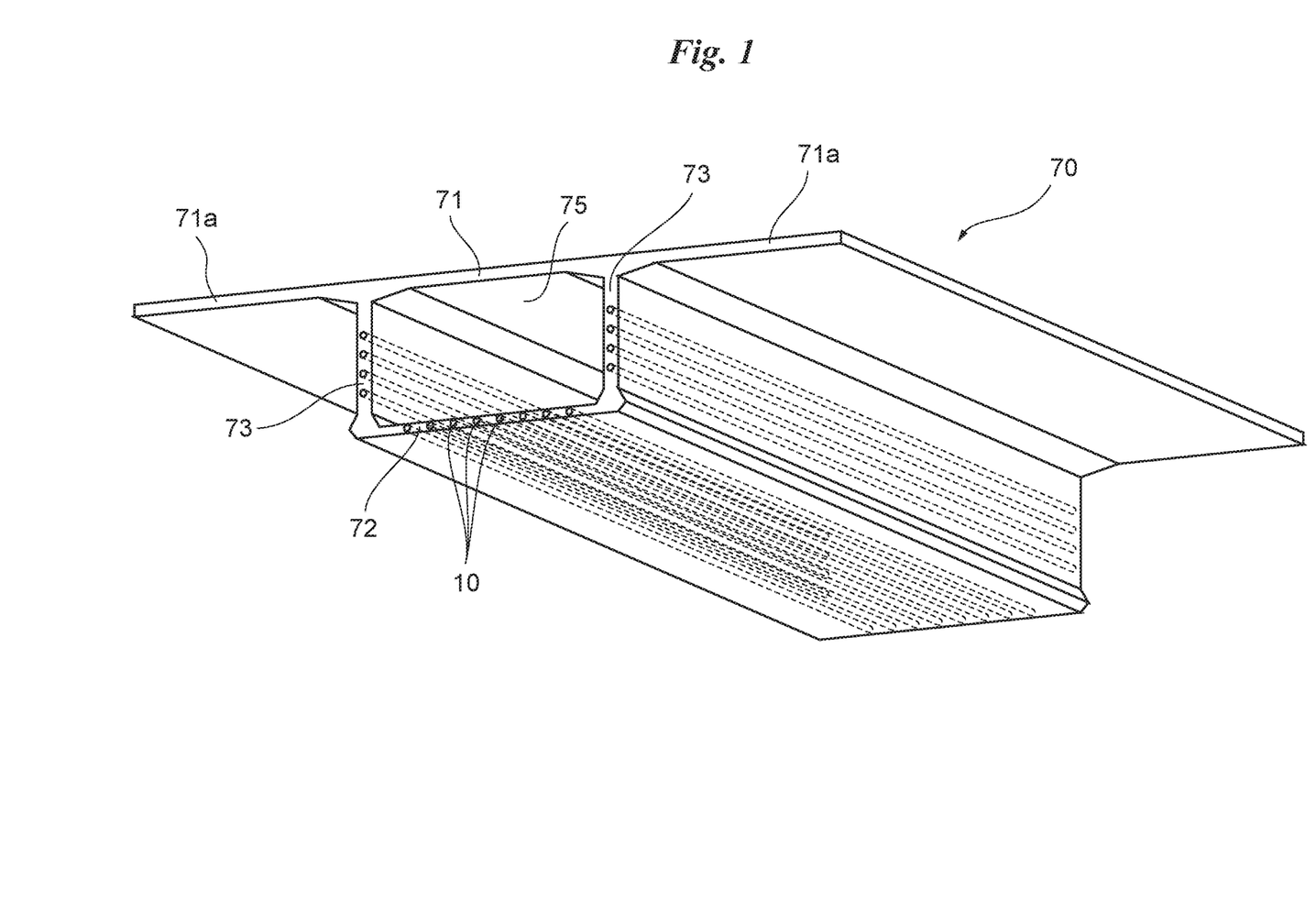
FIG. 1 is a perspective view in which a box girder constituting a concrete box-girder bridge is seen from below.

FIG. 1 is a perspective view in which a box girder constituting a concrete box-girder bridge is seen from below.

The concrete box-girder bridge is fabricated by joining multiple concrete girders 70, made of concrete, along the axial direction of the bridge. The girder 70 is composed of an upper flange 71, a lower flange 72 provided below the upper flange 71 substantially in parallel with the upper flange 71 and spaced away therefrom, and webs 73 connecting respectively each of both side portions of the upper flange 71 and lower flange 72. A space 75 extending along the axial direction of the bridge and enclosed by the upper flange 71, lower flange 72 and webs 73 on both sides is large enough to allow entry of a person so that the concrete box-girder bridge (girder 70) can be inspected from within the space 75. Both sides of the upper flange 71 extend outward sideways from the respective sides, the width of the concrete box-girder bridge being decided by the upper flange 71 and extended portions 71a on both its sides. In general, handrails (not shown) are provided along side edges of the extended portions 71a on the upper surface thereof. The surface of the upper flange 71 and extended portions 71a generally is surfaced with asphalt, and vehicles and pedestrians or the like travel on the asphalt-surfaced upper flange 71 and extended portions 71a.

Multiple steel tendons 10 are embedded inside the concrete lower flange 72 and webs 73, which constitute the girder 70, and they extend along the axial direction of the bridge. The tendons 10, which are used to impart the concrete with compressive stress, are made of steel wire, steel rods or stranded steel wire, these being ferromagnetic bodies the main component of which is iron.

The tendons 10 embedded in the lower flange 72 and webs 73 are inspected one at a time by a damage evaluation apparatus, described next.

Figure 2:
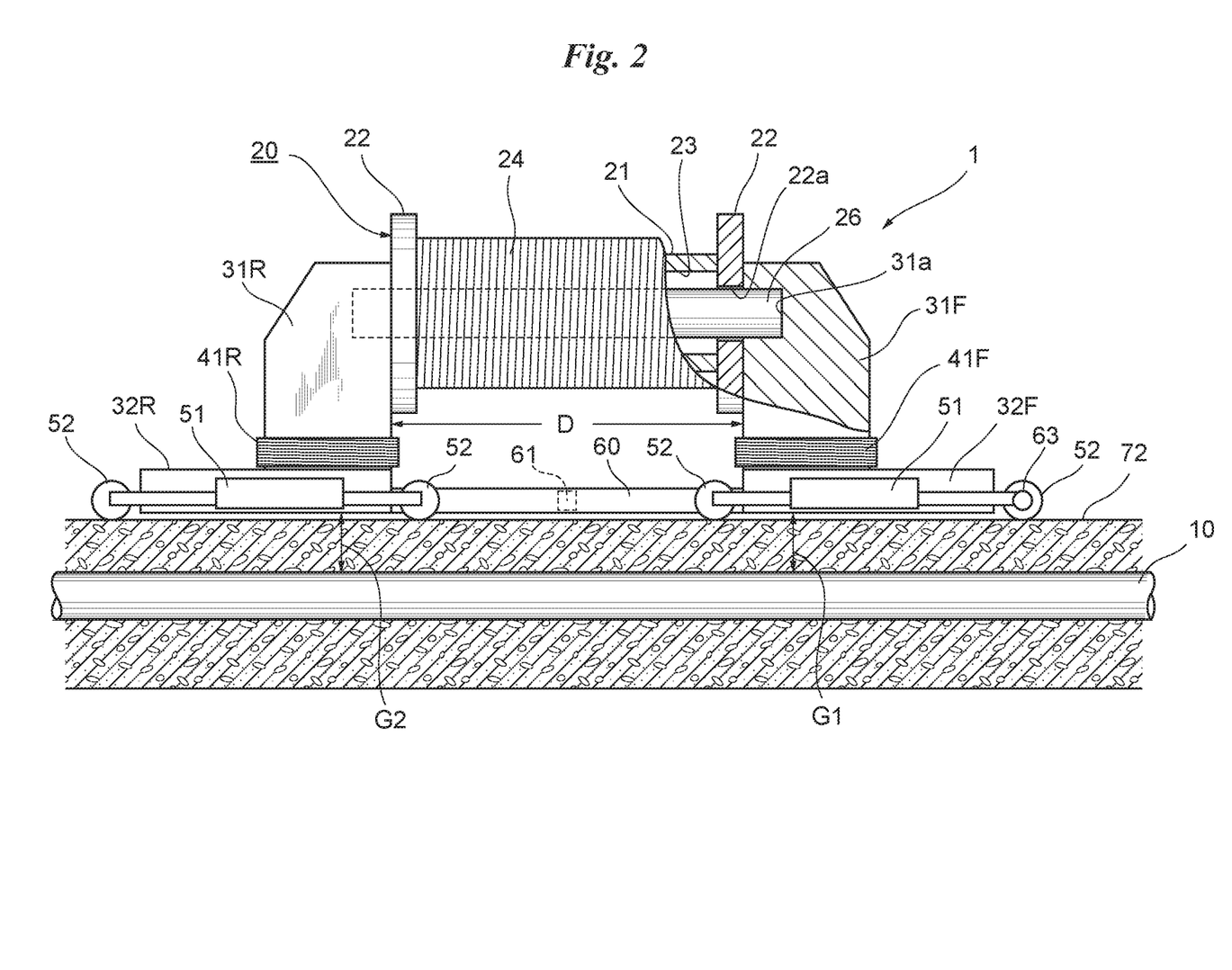
FIG. 2 is a partially cut-away side view of a damage evaluation apparatus.
Figure 3:
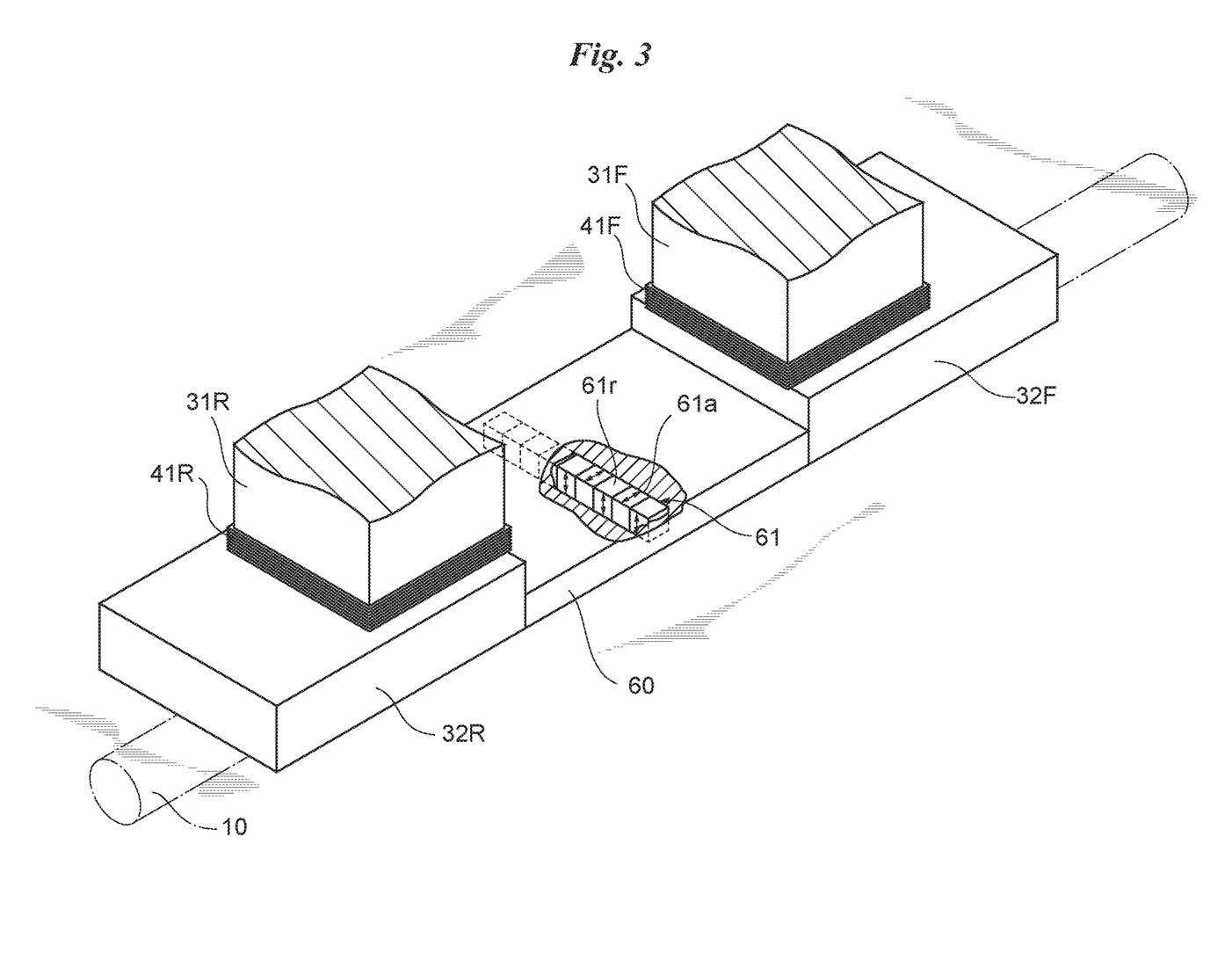
FIG. 3 is an enlarged perspective view partially illustrating a lower portion of the damage evaluation apparatus.

FIG. 2 illustrates a damage evaluation apparatus 1, partially cut away and seen from the side, placed on the surface of the concrete (e.g., on the concrete lower flange 72 constituting the above-mentioned girder 70) in which the tendon 10 has been embedded. FIG. 3 is an enlarged perspective view partially illustrating a lower portion of the damage evaluation apparatus 1. In order to facilitate understanding, a mechanism for moving the damage evaluation apparatus 1, described later, is not illustrated in FIG. 3.

With reference to FIG. 2, damage evaluation apparatus 1 is equipped with a magnetizer 20 for magnetizing a portion of tendon 10 in order to form a magnetic circuit that includes the tendon 10. The magnetizer 20 has a cylindrical bobbin 21; annular flanges 22 secured to respective ones of both ends of the bobbin; an excitation coil 24 wound around the peripheral surface of the bobbin 21 over the entirety of the bobbin between the annular flanges 22 on both ends thereof; an iron core (yoke shaft) 26, which has a circular cross-section, passed through a center hole 23 of the bobbin 21; a pair of columnar yokes 31F, 31R removably secured to the outer surface of respective ones of the two annular flanges 22 and extending downward from both ends of the bobbin 21 (excitation coil 24); and plate-shaped yokes 32F, 32R removably secured to the columnar yokes 31F, 31R, respectively, at a distal end (lower face) thereof.

The damage evaluation apparatus 1 is placed on the concrete surface so as to bring into agreement the axial direction of the excitation coil 24, which constitutes the magnetizer 20, and the longitudinal direction (axial direction) of the tendon 10 to be inspected, and in such a manner that the excitation coil 24 and tendon 10 are aligned one above the other. The damage evaluation apparatus 1 is adapted so as to be movable along a straight line, as will be described later. Preferably, rails (not shown), which are for moving the damage evaluation apparatus 1 directly above the tendon 10 and along the tendon 10 embedded in the concrete, are placed on the concrete surface in advance.

The center of each of the annular flanges 22 has a through-hole 22a that communicates with the center hole 23 of the bobbin 21. The iron core 26 passes through the center hole 23 of the bobbin 21 and through the through-holes 22a of the annular flanges 22 on both sides, and has such a length that it protrudes to the exterior of the annular flanges 22 on both sides. The iron core 26 is magnetized by a magnetic field generated by passing an electric current through the excitation coil 24.

The columnar yokes 31F, 31R in this embodiment are prism-shaped and removably secured at their upper side face to the outer surface of the respective annular flanges 22. The side face of each of the columnar yokes 31F, 31R secured to the annular flanges 22 is formed to have a cylindrical recess 31a. The ends of the iron core 26 are inserted into the respective cylindrical recesses 31a.

As mentioned above, the columnar yokes 31F, 31R extend downwardly (in the direction toward the concrete surface) from both sides of the bobbin 21 (excitation coil 24), and the plate-shaped yokes 32F, 32R are removably secured to the distal end (lower face) thereof. With reference to FIG. 3, the plate-shaped yokes 32F, 32R are rectangular when viewed in a plane and have spread in the horizontal direction, i.e., along the surface of the concrete.

By way of example, permalloy (an Fe—Ni alloy) having a high permeability or permendur (an Fe—Co alloy) exhibiting a high saturation magnetic flux density is used as the material of the columnar yokes 31F, 31R and plate-shaped yokes 32F, 32R. The columnar yokes 31F, 31R and plate-shaped yokes 32F, 32R may consist of the same material or of different materials. Naturally, comparatively inexpensive carbon steel for mechanical structures can also be used. The size of the magnetomotive force generated by the excitation coil 24 may be adopted as the criterion for selecting the material of the columnar yokes 31F, 31R and plate-shaped yokes 32F, 32R. For example, a material having a high permeability might be selected when the excitation coil 24 (bobbin 21) is small in size and cannot generate a large magnetomotive force, and it is conceivable to select a material exhibiting a high saturation flux density in a case where the excitation coil 24 (bobbin 21) is large in size and can generate a large magnetomotive force.

With reference to FIG. 2, frames 51 are secured to the end faces on both sides of each of the plate-shaped yokes 32F, 32R, and rollers 52 are rotatably attached to both ends of each frame 51. The damage evaluation apparatus 1 can be moved linearly along the concrete surface by virtue of the rollers 52.

A rotary encoder 63 (the rotary shaft thereof) is mounted on the rotary shaft of one of the multiple rollers 52, the amount of movement of the damage evaluation apparatus 1 being measured by the rotary encoder 63.

The tendon 10 to be inspected is situated below the bottom face of each of the plate-shaped yokes 32F, 32R (the face facing the concrete surface). A magnetic circuit is formed by the excitation coil 24 (iron core 26), the columnar yoke 31F, the plate-shaped yoke 32F, the tendon 10, which is a ferromagnetic body, the plate-shaped yoke 32R, and the columnar yoke 31R.

Since the tendon 10 is embedded in the concrete, the plate-shaped yokes 32F, 32R are not connected to the tendon 10 and therefore gaps G1, G2 exist between the yokes and tendon. The gaps G1, G2 can be considered as magnetic resistance in the magnetic circuit.

If we let F represent the magnetomotive force of the excitation coil 24 having the iron core 26, f the total magnetic flux and R the magnetic resistance of the magnetic circuit, then the total flux f will be expressed by Equation 1 below:

$$f = F/R \qquad \text{Equation 1}$$

If we let L represent the length of each of the gaps G1, G2 and A the cross-sectional area of each of the gaps, then the magnetic resistance R will be given by Equation 2 below:

$$R = L/\mu A \qquad \text{Equation 2}$$

where $\mu$ is the permeability of the magnetic path of the gaps G1, G2, which here is the permeability of the concrete and the very small clearance (air) between the plate-shaped yokes 32F, 32R and the surface of the concrete.

In view of Equation 2, the larger the cross-sectional area A in the gaps G1, G2, the smaller the magnetic resistance R in the magnetic circuit can be made. As set forth above, the spread-out plate-shaped yokes 32F, 32R are provided on the distal end of the respective columnar yokes 31F, 31R, and thus the gaps G1, G2 are imparted with a large cross-sectional area. As a result, it is possible to reduce the magnetic resistance in the magnetic circuit formed by the excitation coil 24 (iron core 26), the columnar yoke 31F, the plate-shaped yoke 32F, the tendon 10, the plate-shaped yoke 32R, and the columnar yoke 31R, and loss of magnetomotive force in the excitation coil 24 can be reduced. Further, by enlarging the cross-sectional area of the gaps G1, G2 by using the plate-shaped yokes 32F, 32R, the weight of the damage evaluation apparatus 1 can be reduced in comparison with a case where the cross-sectional area of the gaps G1, G2 is enlarged as by using columnar yokes 31F, 31R that are thick.

Further, with the damage evaluation apparatus 1, one of the plate-shaped yokes 32F, 32R forms a N pole and the other forms a S pole. The fact that the distance between the opposing surfaces of the plate-shaped yokes 32F, 32R (which in this embodiment is also the distance between the opposing surfaces of the columnar yokes 31F, 31R), namely a distance D between the poles, is made sufficiently greater than the length of the gaps G1, G2 is also a characterizing feature. Since the magnetic resistance between the magnetic poles (between the plate-shaped yokes 32F, 32R and between the columnar yokes 31F, 31R) can be made greater than the magnetic resistance in the gaps G1, G2 between the plate-shaped yokes 32F, 32R and tendon 10, the magnetic flux that flows directly between the magnetic poles can be eliminated or made small. This also contributes to reducing the loss of magnetomotive force in the magnetic circuit that includes the tendon 10. It is preferred to assure a pole-to-pole distance D that is several times, for example three to ten times, the length of the gaps G1, G2.

The damage evaluation apparatus has two types of magnetic sensor units.

With reference to FIGS. 2 and 3, a first magnetic sensor unit consists of search coils 41F, 41R wound around the respective columnar yokes 31F, 31R in the vicinity of the base end of each. If the tendon 10 sustains a reduction in cross-sectional area due to abrasion or corrosion or develops a gap due to severance, magnetic resistance in the magnetic circuit increases. An increase in magnetic resistance causes a change in magnetic flux that flows through the magnetic circuit. Since the search coils 41F, 41R are wound around the columnar yokes 31F, 31R that form the magnetic path of the magnetic circuit, the magnetic flux that flows through the magnetic circuit interlinks with the search coils 41F, 41R, and the search coils 41F, 41R generate electromotive force conforming to the change in the magnetic flux linkage. Damage that has occurred in the tendon 10 can be evaluated quantitatively based upon output signals from the search coils 41F, 41R and damage evaluation, which is of total-flux measurement type using so-called "return flux", can be carried out. The average value of the output signals from the search coils 41F, 41R may be used in evaluating damage, or the two search coils 41F, 41R may be differentially connected and a single output signal from one of the two search coils 41F, 41R used in evaluating damage. It may be arranged so that only either one of the search coils 41F, 41R is provided.

A second magnetic sensor unit consists of a Hall device group 61 provided between the magnetic poles (between the plate-shaped yokes 32F, 32R). A plate-shaped support member 60 is secured to the opposing faces of the plate-shaped yokes 32F, 32R, and the Hall device group 61 is provided inside the support member 60. The Hall device group 61 includes a plurality of Hall devices 61a, 61r arrayed linearly along the concrete surface in a direction orthogonal to the direction of the axis at the center of the excitation coil 24 (the axial direction of the tendon 10). The Hall devices 61a, 61r output voltages proportional to magnetic flux density.

The Hall devices 61a, 61r are identical devices but they are arranged to have different response orientations. That is, the Hall devices 61r are arranged to have an orientation responsive to magnetic flux in the radial direction of the tendon 10 (direction orthogonal to the concrete surface), and the Hall devices 61a are arranged to have an orientation responsive to magnetic flux along the axial direction of the tendon 10. The response orientations are indicated by the double-ended arrow symbols in FIG. 3. The Hall device group 61 is constructed by arraying the Hall devices 61a, 61r of the mutually different response orientations alternatingly along a straight line.

If the tendon 10 has damage, a disturbance is produced in the magnetic flux passing through the tendon 10 and a portion of the magnetic flux leaks to the outside. Since the leakage magnetic flux contains a large component in the radial direction of the tendon 10, output signals are generated by the Hall devices 61r whose response orientation is made the radial direction of the tendon 10. Based upon the output signals from the Hall devices 61r, whether the tendon 10 is damaged and, if so, the extent of the damage, can be detected.

The Hall devices 61a whose response orientation is made the axial direction of the tendon 10 can accurately detect magnetic flux in the axial direction at the periphery of the tendon 10. Since the plurality of Hall devices 61a are arrayed in a row in a direction orthogonal to the axial direction of the tendon 10 (the direction of movement of the damage evaluation apparatus 1 is decided so as to obtain this direction), the distances between the tendon 10 and the plurality of Hall devices 61a will differ for each one of the Hall devices 61a and, hence, large output signals are output from the Hall devices 61a close to the tendon 10 and small output signals are output from the Hall devices 61a distant from the tendon 10. The travel path of the damage evaluation apparatus 1 can be decided by comparing the output signals from the plurality of Hall devices 61a. Typically, the travel path of the damage evaluation apparatus 1 is decided in such a manner that, from among the plurality of Hall devices 61a arrayed in the row, the output signals from the Hall devices 61a situated centrally are maximized, i.e., in such a manner that the tendon 10 will be situated centrally of the damage evaluation apparatus 1 in the width direction thereof. As a result, more stable signal acquisition is achieved.

Preferably, the Hall device group 61 that includes the multiple Hall devices 61a, 61r is provided at a position midway between the plate-shaped yokes 32F, 32R, namely at a position midway between the magnetic poles. Since the magnetic field at the position midway between the magnetic poles is more stable in comparison with the magnetic field at a location near either of the plate-shaped yokes 32F, 32R, the accuracy with which the leakage magnetic flux is detected can be improved.

Figure 4:
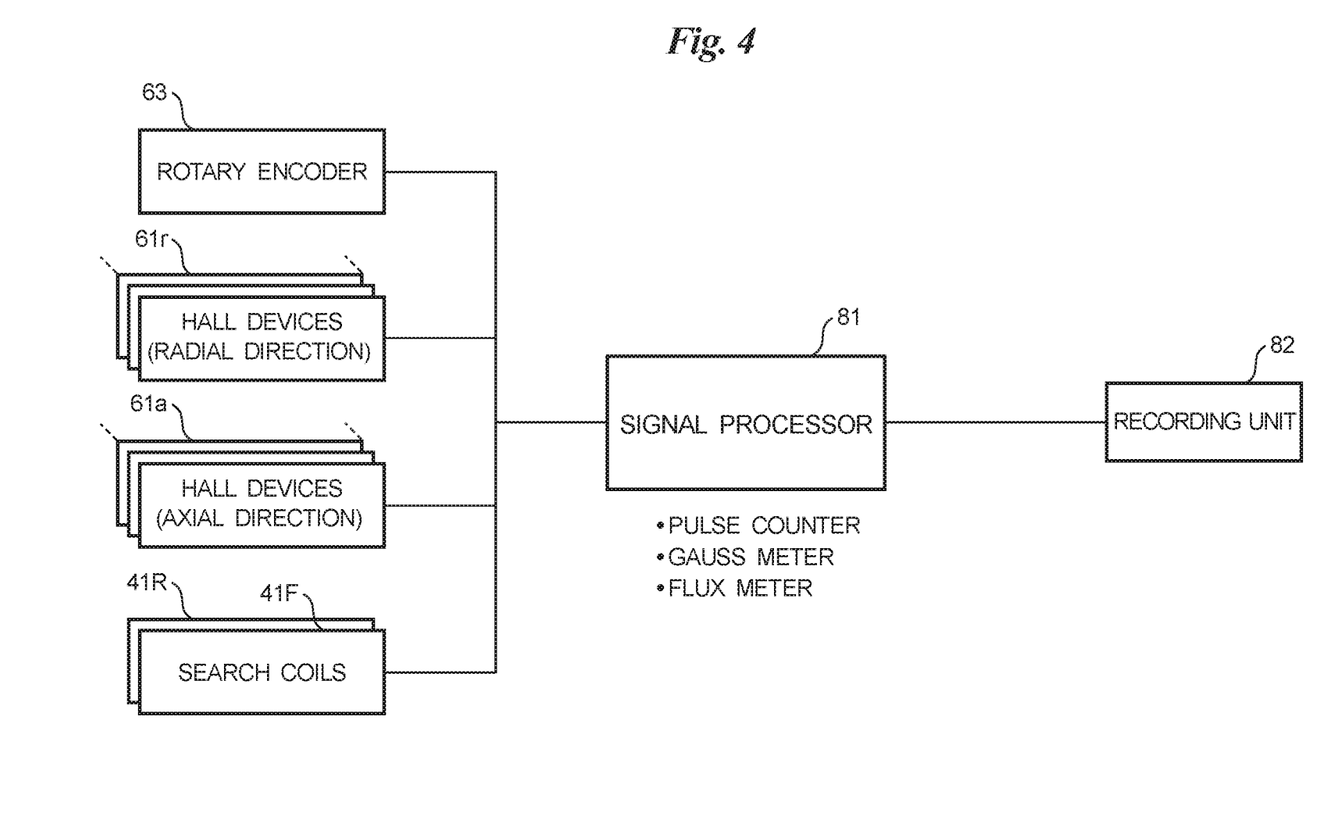
FIG. 4 is a block diagram illustrating the electrical configuration of a processing unit for processing signals output from a group of sensors.

FIG. 4 is a block diagram illustrating the electrical configuration of a processing unit for processing signals output from the group of sensors (the rotary encoder 63, the Hall devices 61r responsive to the magnetic flux in the radial direction of the tendon 10, the Hall devices 61a responsive to the magnetic flux in the axial direction of the tendon 10, and the search coils 41F, 41R) with which the damage evaluation apparatus 1 is equipped.

The rotary encoder 63 provided on the roller 52 for moving the damage evaluation apparatus 1 outputs a pulse signal conforming to the rotation of the roller 52, and the signal is applied to a signal processor 81. The signal processor 81 has a pulse counter and calculates data, which is indicative of the amount of movement of the damage evaluation apparatus 1, from the amount of movement per pulse and the number of pulses. The data indicating the amount of movement is recorded in a recording unit 82.

The Hall devices 61a, 61r are connected to a Gauss meter (Tesla meter) possessed by the signal processor 81. As mentioned above, the Hall devices 61a, 61r output voltages proportional to magnetic flux density. Based upon the output voltages from the Hall devices 61a, 61r, the signal processor 81 calculates magnetic flux density and applies it to the recording unit 82.

The greater the extent of damage to the tendon 10, the larger the value of the magnetic flux density of the leakage flux. The change in magnetic flux density, therefore, which is calculated based upon the output voltages from the Hall devices 61r that are responsive to the magnetic flux in the radial direction of the tendon 10, can be used to judge whether the tendon 10 is damaged as well as the extent of any such damage. Further, since the data indicating amount of movement detected by the rotary encoder 63 also is recorded in the recording unit 82, the position of the damage that has occurred in the tendon 10 can be found as well. By way of example, the average value of magnetic flux density calculated based upon the output voltages from respective ones of the plurality of Hall devices 61r is recorded in the recording unit 82 at predetermined times.

With regard to magnetic flux density calculated based upon the output voltages from the Hall devices 61a, this can be used to decide the path of travel of the damage evaluation apparatus 1, as mentioned above. Each magnetic flux density calculated based upon the output voltages from the plurality of Hall devices 61a is recorded in the recording unit 82.

It goes without saying that the voltage values that are output from the Hall devices 61r, 61a may be recorded in the recording unit 82. Magnetic flux density is calculated as necessary in the signal processor 81 from the voltage values recorded in the recording unit 82.

The search coils 41F, 41R provided in the magnetic path of the magnetic circuit are connected to a flux meter possessed by the signal processor 81. Voltages produced in the search coils 41F, 41R owing to a change in magnetic flux are integrated over time in the flux meter, whereby the magnetic flux (number of magnetic flux linkages) is calculated. This is applied to the recording unit 82. Damage that has occurred in the tendon 10 can be determined quantitatively based upon the change in magnetic flux.

Figure 5:
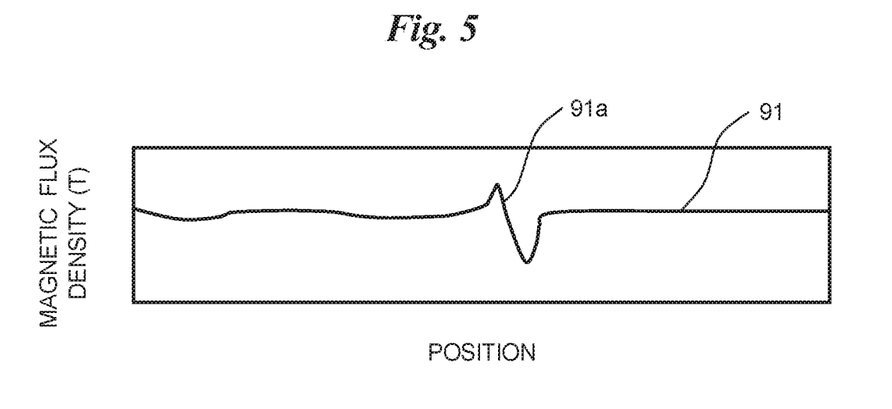
FIG. 5, which illustrates the result of inspection of a corroded tendon, is a graph of magnetic flux density calculated based upon output voltage that is output from a Hall device responsive to magnetic flux in the radial direction of the tendon.
Figure 6:
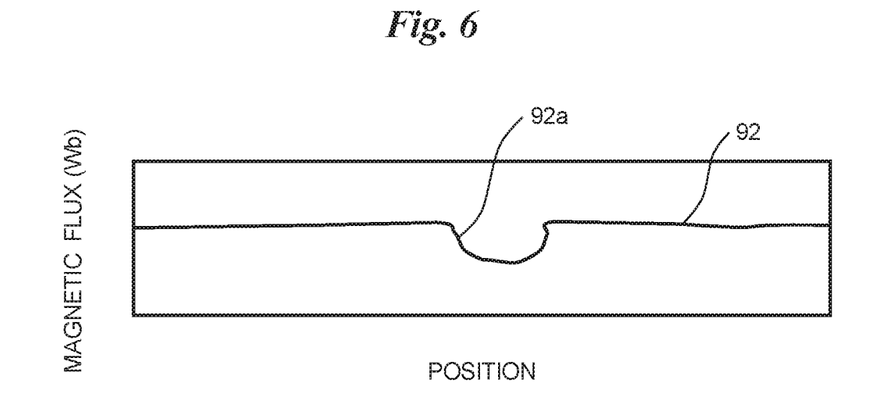
FIG. 6, which illustrates the result of inspection of a corroded tendon, is a graph of magnetic flux density calculated based upon output voltage that is output from a search coil.
Figure 7:
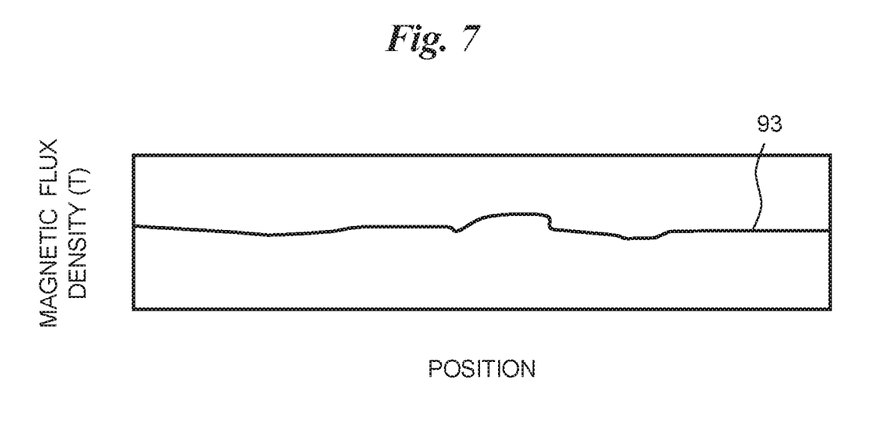
FIG. 7, which illustrates the result of inspection of a corroded tendon, is a graph of magnetic flux density calculated based upon output voltage that is output from a Hall device responsive to magnetic flux in the axial direction of the tendon.

FIGS. 5 to 7 illustrate waveforms of signals recorded in the recording unit 82 when the damage evaluation apparatus 1 is moved along the tendon 10 on the surface of the concrete in which the tendon 10, a portion of which has corroded, is embedded. In FIGS. 5 to 7, the horizontal axis indicates the position (amount of movement) of the damage evaluation apparatus 1 detected by the rotary encoder 63.

FIG. 5 illustrates a signal waveform 91 of magnetic flux density calculated based upon the output voltages from the Hall devices 61r responsive to magnetic flux in the radial direction of the tendon 10. If the tendon 10 has corrosion, an increase and decrease (the portion of the signal waveform indicated at 91a) in the magnetic flux density will be observed in the signal waveform 91 which prevails when the corroded area passes by the Hall devices 61*r*.

FIG. 6 illustrates a signal waveform 92 of magnetic flux (number of magnetic flux linkages) calculated based upon the output voltages from the search coils 41F, 41R. If the tendon 10 has corrosion, a decrease (the portion of the signal waveform indicated at 92*a*) in the magnetic flux will be observed in the signal waveform 92 during the time the corroded area is sandwiched between the magnetic poles.

For reference purposes, FIG. 7 illustrates a signal waveform 93 of magnetic flux density calculated based upon the output voltages from the Hall devices 61*a* responsive to magnetic flux in the axial direction of the tendon 10.

The Hall devices 61*r* responsive to magnetic flux in the axial direction of the tendon 10 exhibit a high detection sensitivity to damage that has occurred locally in the tendon 10, whereas the search coils 41F, 41R that sense a change in the magnetic flux that flows through the magnetic circuit exhibit a high detection sensitivity to damage that has occurred over a comparatively wide area. In order to evaluate deterioration of the tendon 10 within the concrete, it is preferred that both the Hall devices 61*r* and search coils 41F, 41R be provided. Evaluation of deterioration of the tendon 10 within the concrete can of course be performed even if only either one of the above, namely either only the Hall devices 61*r* or only the search coils 41F, 41R, are provided.

In the embodiments described above, leakage magnetic flux is detected using the Hall devices 61*r* and total magnetic flux (magnetic flux that flows through the magnetic circuit) is detected using the search coils 41F, 41R. However, leakage magnetic flux can also be detected using search coils instead of the Hall devices 61*r* (the search coils would be provided at the position where the Hall devices 61*r* are placed), and magnetic flux (total magnetic flux) that flows through the magnetic circuit can also be detected using Hall devices instead of the search coils 41F, 41R (the Hall devices would be provided on the bottom surface of the plate-shaped yokes 32F, 32R).

The invention claimed is:

1. A method of evaluating damage to a magnetic linear body, comprising:
    moving a damage evaluation apparatus along the magnetic linear body, on a concrete structure in which the magnetic linear body, which is to undergo evaluation of damage, is embedded, said apparatus including a magnetizer for generating magnetic force, and a detector for detecting an amount of change in magnetism produced from a damaged area of the magnetic linear body magnetized by the magnetic force generated by the magnetizer;
    forming a magnetic circuit by passing an electric current through an excitation coil by the magnetizer, wherein said magnetizer includes said excitation coil as well as a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, said magnetic circuit including the yoke shaft, the pair of columnar yokes, the pair of plate-shaped yokes and the magnetic linear body over a range thereof situated between the pair of plate-shaped yokes; and
    detecting magnetic flux, which flows through the magnetic circuit, by the detector.

2. The method of evaluating damage to a magnetic linear body according to claim 1, wherein said detector is a search coil wound around at least one of the pair of columnar yokes.

3. The method of evaluating damage to a magnetic linear body according to claim 1, wherein said detector is a Hall device secured to a bottom surface of the plate-shaped yokes.

4. The method of evaluating damage to a magnetic linear body according to claim 1, wherein distance between the pair of plate-shaped yokes is longer than distance from the bottom surface of the pair of plate-shaped yokes to the magnetic linear body.

5. The method of evaluating damage to a magnetic linear body according to claim 1, wherein said damage evaluation apparatus has a position detecting device for detecting position of the damage evaluation apparatus relative to the magnetic linear body, path of travel of the damage evaluation apparatus being decided in accordance with an output from the position detecting device.

6. A method of evaluating damage to a magnetic linear body, comprising:
    moving a damage evaluation apparatus along the magnetic linear body, on a concrete structure in which the magnetic linear body, which is to undergo evaluation of damage, is embedded, said apparatus including a magnetizer for generating magnetic force, and a detector for detecting an amount of change in magnetism produced from a damaged area of the magnetic linear body magnetized by the magnetic force generated by the magnetizer;
    forming a magnetic circuit by passing an electric current through an excitation coil by the magnetizer, wherein said magnetizer includes said excitation coil as well as a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, said magnetic circuit including the yoke shaft, the pair of columnar yokes, the pair of plate-shaped yokes and the magnetic linear body over a range thereof situated between the pair of plate-shaped yokes; and
    detecting magnetic flux, which leaks from the damaged area of the magnetic linear body, by the detector.

7. The method of evaluating damage to a magnetic linear body according to claim 6, wherein distance between the pair of plate-shaped yokes is longer than distance from the bottom surface of the pair of plate-shaped yokes to the magnetic linear body.

8. The method of evaluating damage to a magnetic linear body according to claim 6, wherein said detector is provided at a position midway between the plate-shaped yokes.

9. The method of evaluating damage to a magnetic linear body according to claim 6, wherein said detector is a Hall device.

10. The method of evaluating damage to a magnetic linear body according to claim 9, wherein a plurality of the Hall devices having an orientation responsive to magnetic flux along the radial direction of the magnetic linear body are arrayed in a row in a direction orthogonal to the direction of the central axis of the excitation coil.

11. The method of evaluating damage to a magnetic linear body according to claim 6, wherein said detector is a search coil.

12. The method of evaluating damage to a magnetic linear body according to claim 6, wherein said damage evaluation apparatus has a position detecting device for detecting position of the damage evaluation apparatus relative to the magnetic linear body, path of travel of the damage evaluation apparatus being decided in accordance with an output from the position detecting device.

13. The method of evaluating damage to a magnetic linear body according to claim 12, wherein said position detecting device is a plurality of Hall devices, arrayed in a row in a direction orthogonal to the direction of the central axis of the excitation coil, having an orientation responsive to magnetic flux along the axial direction of the magnetic linear body.

14. An apparatus for evaluating damage to a magnetic linear body is used upon being placed on a concrete structure in which the magnetic linear body, which is to undergo evaluation of damage, is embedded, and includes a magnetizer for generating magnetic force, and a detector for detecting an amount of change in magnetism produced from a damaged area of the magnetic linear body magnetized by the magnetic force generated by the magnetizer;

said apparatus having a moving device, which includes a movement amount sensor, for moving said damage evaluation apparatus along the magnetic linear body;

wherein said magnetizer includes an excitation coil, a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, and passes an electric current through the excitation coil, whereby a magnetic circuit is formed by the yoke shaft, the pair of columnar yokes, the pair of plate-shaped yokes and the magnetic linear body over a range thereof situated between the pair of plate-shaped yokes;

said detector being a magnetic flux detector for detecting magnetic flux that flows through the magnetic circuit.

15. The apparatus for evaluating damage to a magnetic linear body according to claim 14, wherein distance between the pair of plate-shaped yokes is longer than distance from the bottom surface of the pair of plate-shaped yokes to the magnetic linear body.

16. The apparatus for evaluating damage to a magnetic linear body according to claim 14, wherein said apparatus is provided with a position detecting device for detecting the position of said apparatus relative to the magnetic linear body.

17. An apparatus for evaluating damage to a magnetic linear body is used upon being placed on a concrete structure in which the magnetic linear body, which is to undergo evaluation of damage, is embedded, and includes a magnetizer for generating magnetic force, and a detector for detecting an amount of change in magnetism produced from a damaged area of the magnetic linear body magnetized by the magnetic force generated by the magnetizer;

said apparatus having a moving device, which includes a movement amount sensor, for moving said damage evaluation apparatus along the magnetic linear body;

wherein said magnetizer includes an excitation coil, a yoke shaft inserted into a center hole of the excitation coil, a pair of columnar yokes connected to respective ones of both ends of the yoke shaft and each extending toward the surface of the concrete, and a pair of plate-shaped yokes connected to respective ones of the pair of columnar yokes at a distal end thereof for forming magnetic poles having spread along the surface of the concrete, and passes an electric current through the excitation coil, whereby a magnetic circuit is formed by the yoke shaft, the pair of columnar yokes, the pair of plate-shaped yokes and the magnetic linear body over a range thereof situated between the pair of plate-shaped yokes;

said detector being a leakage magnetic flux detector for detecting magnetic flux that leaks from the damages area of the magnetic linear body.

18. The apparatus for evaluating damage to a magnetic linear body according to claim 17, wherein distance between the pair of plate-shaped yokes is longer than distance from the bottom surface of the pair of plate-shaped yokes to the magnetic linear body.

19. The apparatus for evaluating damage to a magnetic linear body according to claim 17, wherein said apparatus is provided with a position detecting device for detecting the position of said apparatus relative to the magnetic linear body.

20. The apparatus for evaluating damage to a magnetic linear body according to claim 19, wherein said position detecting device is a plurality of Hall devices, arrayed in a row in a direction orthogonal to the direction of the central axis of the excitation coil, having an orientation responsive to magnetic flux along the axial direction of the magnetic linear body.

* * * * *